United States Patent
Elliott et al.

(10) Patent No.: US 6,936,242 B2
(45) Date of Patent: Aug. 30, 2005

(54) MULTI-PORTION ANTIPERSPIRANT COMPOSITION

(75) Inventors: David L. Elliott, North Attleboro, MA (US); Dennis J. Colwell, Mansfield, MA (US); Jayant N. Sane, Framingham, MA (US); Tuan M. Vu, Canton, MA (US); Cheryl Lynn Galante, Marshfield, MA (US)

(73) Assignee: The Gillette Company, Boston, MA (US)

( * ) Notice: Subject to any disclaimer, the term of this patent is extended or adjusted under 35 U.S.C. 154(b) by 267 days.

(21) Appl. No.: 10/298,113

(22) Filed: Nov. 15, 2002

(65) Prior Publication Data

US 2004/0096408 A1 May 20, 2004

(51) Int. Cl.[7] .............................. A61K 7/32; A61K 7/00
(52) U.S. Cl. .......................... 424/65; 424/400; 424/401
(58) Field of Search ........................... 424/65, 400, 401

(56) References Cited

U.S. PATENT DOCUMENTS

| | | | |
|---|---|---|---|
| 4,120,948 A | 10/1978 | Shelton | 424/66 |
| 5,384,117 A | 1/1995 | Vu et al. | 424/66 |
| 5,744,130 A * | 4/1998 | Guskey et al. | 424/66 |
| 5,972,319 A | 10/1999 | Linn et al. | 424/65 |

FOREIGN PATENT DOCUMENTS

| | | |
|---|---|---|
| CA | 2309334 | 10/1998 |
| DE | 199 21 183 | 11/2000 |
| WO | WO 01/58411 | 8/2001 |
| WO | WO 02/065998 | 8/2002 |

\* cited by examiner

*Primary Examiner*—Shelley A. Dodson
(74) *Attorney, Agent, or Firm*—Stepan P. Williams

(57) ABSTRACT

Disclosed is a non-flowable anhydrous topical antiperspirant composition comprising a first portion and a second portion contiguous with the first portion. The first portion is semi-opaque to opaque and comprises a first hydrophobic carrier vehicle and a first gellant and has a particulate antiperspirant active suspended therein. The second portion is translucent to transparent and comprises a second hydrophobic carrier vehicle and a second gellant. Preferably, the second hydrophobic carrier vehicle has an average refractive index that approximately matches the refractive index of the second gellant. Ideally, for greater translucency the second portion will be substantially free of antiperspirant salt and/or other opacifying materials. Preferably, the first hydrophobic carrier vehicle also has an average refractive index that approximately matches the refractive index of the first gellant. Even more preferably, the second hydrophobic carrier vehicle and second gellant are comprised of substantially the same materials in substantially the same proportions as the first hydrophobic carrier vehicle and first gellant.

21 Claims, 1 Drawing Sheet

MULTI-PORTION ANTIPERSPIRANT COMPOSITION

BACKGROUND OF THE INVENTION

The present invention relates to a non-flowable anhydrous topical antiperspirant composition comprising a first portion and a second portion contiguous with the first portion.

In WO 02/065998 there is described an antiperspirant product that includes two portions having different compositions. One embodiment includes a product having an application surface where one of the portions is in the form of a stripe that extends across the application surface approximately centrally through the other portion. One of the portions may be opaque and the other portion may be clear. Two ways of achieving clarity are described. In one, dibenzylidene sorbitol is used as the gelling agent to gel a polyhydric alcohol vehicle. In another, it is suggested to use a water-in-oil emulsion wherein the refractive index of the water phase is matched to the refractive index of the oil phase. In each of these systems, the antiperspirant salt is dissolved in the vehicle used in the clear portion.

In U.S. Pat. No. 4,120,948 there is described a two-phase antiperspirant stick composition having a shell and core structure. The core includes a particulate antiperspirant active suspended in a hydrophobic carrier gelled with a wax gelling agent. The shell includes a polyhydric alcohol gelled with a fatty acid soap, such as sodium stearate, or a fatty acid amide. The gel phase does not include antiperspirant salt. In DE 199 21 183 there is also described an antiperspirant stick composition having a shell and core structure. While the composition of the shell and core are said to be different, both include a hydrophobic liquid carrier, such as a silicone, that is solidified with a conventional gelling agent. One or both phases may include an antiperspirant salt suspended therein. There is no suggestion that either phase can be made translucent and, in the formulations exemplified, both phases are opaque.

In U.S. Pat. No. 5,384,117 there is described a clear anhydrous suspension-type antiperspirant stick composition in which the refractive index of the vehicle is matched to the refractive index of the antiperspirant salt. The gelling agent must also have a suitably matched refractive index. Examples of suitable gelling agents include polyethylene-vinyl acetate copolymer and polyethylene homopolymer. Similarly, in WO 01/058411 there is described a soft-solid antiperspirant composition in which the refractive index of the vehicle is approximately matched to the refractive index of the suspended antiperspirant salt, so that they differ by no more than 0.08. In this way, it is suggested that a ribbon of the composition dispensed through a narrow aperture will have a translucent appearance even though the gross formulation may be opaque.

In U.S. Pat. No. 5,972,319 and U.S. Pat. No. 6,361,766, there are described anhydrous antiperspirant compositions that contain a substantial amount of an emollient with a high refractive index to reduce whitening. The former suggests the use of emollients with a refractive index greater than about 1.446, while the latter suggests emollients with a refractive index greater than about 1.465.

It would be desirable to provide an antiperspirant composition having at least two contiguous portions, such as, for example, a striped antiperspirant product, wherein the composition has improved aesthetic properties, particularly an improved aesthetic appearance. In particular, it would be desirable to provide such a composition wherein one of the portions is translucent to transparent, but which does not require the use of a polyhydric alcohol/dibenzylidene sorbitol system or a water-in-oil emulsion system. In other words, it would be desirable to provide a translucent to transparent portion in which the carrier vehicle is a hydrophobic material such as a silicone or an organic oil.

In addition, it would be highly desirable to provide an antiperspirant composition having at least two contiguous portions wherein the portions are balanced compositionally so as to minimize migration of components from one portion to the other. Such migration, which readily occurs when one portion is compositionally different from the other portion (i.e. unbalanced), causes the product to become unstable and/or aesthetically unacceptable. For example, initial translucency or clarity can be lost over time.

SUMMARY OF THE INVENTION

The present invention embraces a non-flowable anhydrous topical antiperspirant composition comprising a first portion and a second portion contiguous with the first portion. The first portion is semi-opaque to opaque and comprises a first hydrophobic carrier vehicle and a first gellant and has a particulate antiperspirant active suspended therein. The second portion is translucent to transparent and comprises a second hydrophobic carrier vehicle and a second gellant. Preferably, the second hydrophobic carrier vehicle has an average refractive index that approximately matches the refractive index of the second gellant. Ideally, for greater translucency the second portion will be substantially free of antiperspirant salt and/or other opacifying materials. Preferably, the first hydrophobic carrier vehicle also has an average refractive index that approximately matches the refractive index of the first gellant. Even more preferably, the second hydrophobic carrier vehicle and second gellant are comprised of substantially the same materials in substantially the same proportions as the first hydrophobic carrier vehicle and first gellant. The present invention also embraces a method of reducing perspiration from human skin by applying to the skin the aforementioned antiperspirant composition.

DETAILED DESCRIPTION OF THE INVENTION

Figure 1:
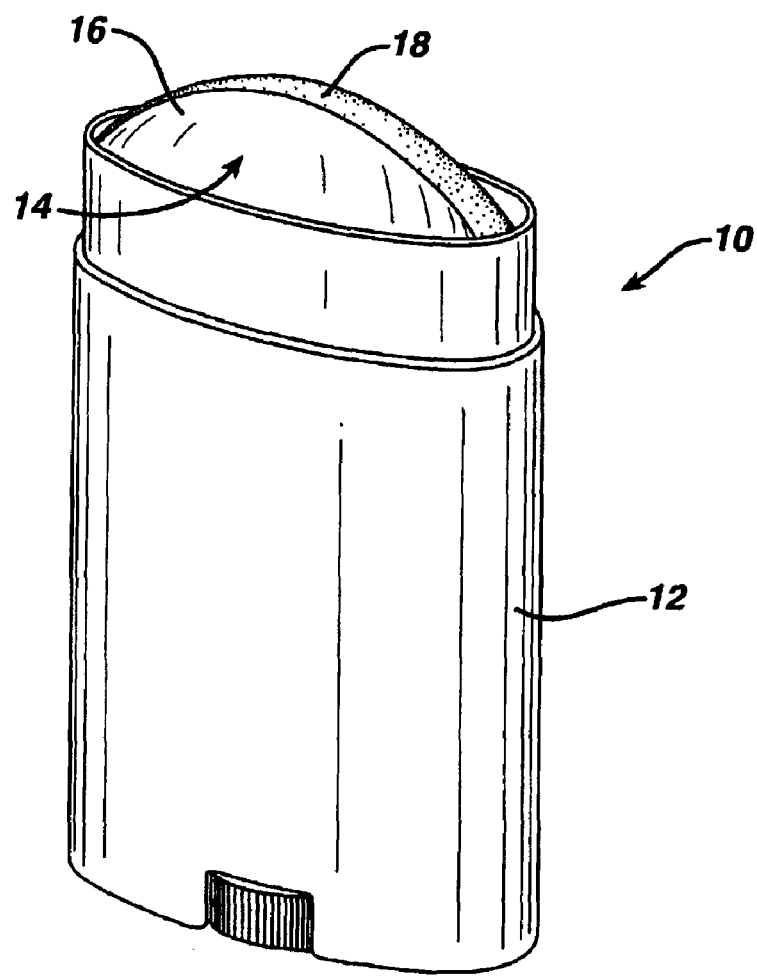
FIG. 1 is a perspective view of an antiperspirant product.

The following definitions will apply throughout the specification and claims to the terms set out below:

"Anhydrous" means substantially free (that is, contains less than about 2%, preferably less than 1%, and most preferably less than 0.1% by weight) of free water (excluding any water of hydration associated with the antiperspirant salt or other components of the composition).

"Portion" means a visually distinct part or section with a defined boundary and a particular composition. Depending on the context, portion (in the singular) may include one or more parts or sections of identical composition. Thus, for example, if a product is constructed with multiple portions of identical composition (e.g., two blue stripes of one composition and three white stripes of a different composition), the term portion may be used to refer to any one of those portions (e.g., one blue stripe or one white stripe) or it may be used to refer to all of those portions of identical composition (e.g., both blue stripes together).

"Contiguous" means in contact or touching. Thus, one portion is contiguous with another portion when it has at least part of its boundary in direct contact with at least part of the boundary of the other portion.

"Different color", when applied to a portion, means that the portion is a different color (e.g., red vs. blue) or a different shade of color (e.g., light green vs. dark green) than the other portion. For purposes of this definition, white and black are considered colors.

"Visually distinct" or "different visual appearance", when applied to a portion, means that the portion can be visually differentiated (by naked eye) from the other portion such as by different light transmittance (e.g., opaque vs. translucent or opaque vs. transparent or translucent vs. transparent) and/or by different color (e.g., red vs. blue or light green vs. dark green).

"Non-flowable", when applied to a composition, means that the composition, at 25° C., does not flow or self-mix, for example, like a liquid, but rather maintains its form unless disturbed by some external force. Examples of non-flowable compositions include medium stiff to very stiff gels or creams (e.g., viscosity greater than 40,000 cP at 20° C.), and soft solids to hard solids (e.g., stick hardness of 80 to 600 grams measured with a TA-XT2 Texture Analyzer (Texture Technologies Corp.) using a cone-shaped needle (TA-17, 30° cone), a cursor speed of 1.0 mm/sec and a penetration distance of 5 mm).

"Translucent" means light-transmitting, but not transparent (optically clear). Translucent portions generally have a % Opacity value (as described below) of about 10% to about 60%, preferably about 10% to about 50%. A translucent portion may exhibit some light diffusion that prevents perception of distinct images through the portion.

"Transparent" means that the composition has a % Opacity value (as described below) of about 0% to about 10%. Ideally, one should be able to perceive words or objects through a 0.5 cm thick section of the composition.

"Semi-opaque" means that the composition has a % Opacity value (as described below) of about 61% to about 90%.

"Opaque" means that the composition has a % Opacity value (as described below) of about 90% to about 100%.

% Opacity is measured using a BYK Gardner (Columbia, Md.) Color-Guide 45/0 hand-held spectrophotometer (Catalog #LCB-6800), which has a standard measurement function for % Opacity. The opacity measurement uses the L*a*b color scale and is based on readings obtained when a 0.25 inch (0.64 cm) thick film of the test material is placed on a standard black background versus a standard white background (standard black and white color sheets from BYK Gardner (Catalog #LAR-3700)). Measurements resulting in 100% opacity (0% clarity) indicate that there is no difference between the material with a black or white background (i.e., no light passes through the test material). Measurements resulting in 0% opacity indicate that all light passes through the test material (i.e., 100% transparent). Generally, four replicate measurements are made and % Opacity is the average of the four measurements.

The present invention embraces a non-flowable anhydrous topical antiperspirant composition comprising a first portion and a second portion contiguous with the first portion. The first portion is semi-opaque to opaque (i.e., about 61% to about 100% opacity) and comprises a first hydrophobic carrier vehicle and a first gellant and has an antiperspirant salt suspended therein. The second portion is translucent to transparent (i.e., about 0% to about 60% opacity) and comprises a second hydrophobic carrier vehicle and a second gellant. As will be described in more detail later, the translucent to transparent appearance of the second portion can be readily obtained by approximately matching (typically to about 0.05 or better) the average refractive index of the second hydrophobic carrier vehicle to the average refractive index of the second gellant. Typically the first portion will comprise 15% to 85%, preferably 50% to 80%, by volume, of the composition and the second portion will comprise 15% to 85%, preferably 20% to 50%, by volume, of the composition. The composition has an application surface and the second portion forms a geometric shape at the application surface, which geometric shape is bordered on at least one side, preferably on at least two sides, by the first portion.

Figure 2:
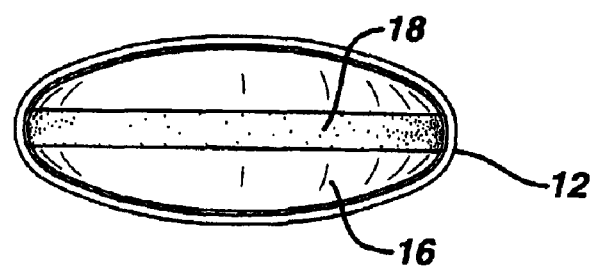
FIG. 2 is a top view of the antiperspirant product shown in FIG. 1.

Referring to FIGS. 1 and 2, an antiperspirant product 10 includes a container 12 and an antiperspirant composition within the container having application surface 14 for application to an underarm. The composition includes first portion 16 and second portion 18 that together define application surface 14. Second portion 18 is a different color than first portion 16 and runs centrally through and divides portion 16, thus providing a striped appearance. In this embodiment, each portion extends at least partially downwardly (not shown) from the application surface toward the bottom of the container in order to provide a renewable application surface of similar appearance as the product is used. Portion 18 can have a width, for example, of at least 0.2 cm, and preferably between 0.4 cm and 1.3 cm. In product 10, portion 18 has a width of about 0.6 cm, which is between 25% and 35% of the application surface. Second portion 18 is translucent or transparent, and first portion 16 is opaque or semi-opaque. Portion 16 includes an antiperspirant salt suspended therein.

Naturally, of course, the portions of a multi-portion antiperspirant product need not be arranged only as depicted in FIGS. 1 and 2, which is merely one possible example of a suitable arrangement. The portions may be arranged in any way desired to provide a particular structure or appearance that may be desirable. For example, portion 18, instead of running longitudinally, could run diagonally across the surface, or even laterally. Alternatively, portion 18 could be wavy or swirled instead of straight. Or, if one desired, there could be two portions 18 that run parallel to each other (e.g., longitudinally or diagonally). In a further embodiment, portion 18 could be a central core (e.g., an oval or circle) surrounded by portion 16. Another possible arrangement is where the first portion 16 and the second portion 18 each comprise approximately half of the application surface. An interesting arrangement is one where portion 18 comprises a plurality of swirled portions interspersed throughout portion 16 in a marbled pattern. Of course, the antiperspirant product may also comprise more than two portions so that in addition to the first portion and the second portion, it could also include a third portion, or even a fourth portion or a fifth portion, etc. Each such portion of a multi-portion product may have a different composition or two of such portions may have the same composition (so long as at least one portion has a different composition from one of the other portions).

The anhydrous topical antiperspirant composition of the present invention includes a particulate antiperspirant active suspended in the first portion. While it is also possible to include an antiperspirant active in the second portion if desired, ideally, for greater translucency, the second portion will be substantially free of antiperspirant active and/or other opacifying materials. A suitable antiperspirant active may be any agent that inhibits or reduces perspiration from the skin, particularly the axilla (underarm). Antiperspirant actives include the aluminum and aluminum-zirconium antiperspirant salts, particularly the enhanced efficacy antiperspirant salts. Preferred compositions of the present invention will comprise, by weight of the total composition, about 3% to about 30%, more preferably about 8% to about 24%, of an aluminum or an aluminum-zirconium antiperspirant salt. The amount of antiperspirant salt contained in the first portion will necessarily be proportionally higher in order to compensate for any portions that do not contain antiperspirant salt. Thus, if the first portion comprises 67% of the total composition, then it will need to contain 35% antiperspirant salt in order for the total composition to contain 23.5% salt (which corresponds to about 18.3% active USP). Ideally, the total composition should contain about 10% to about 20% active (by weight, USP).

Preferred aluminum salts are those having the general formula $Al_2(OH)_{6-a}X_a$ wherein X is Cl, Br, I or $NO_3$, and a is about 0.3 to about 5, preferably about 0.8 to about 2.5, more preferably about 1 to about 2 (such that the Al to X mole ratio is about 0.9:1 to about 2.1:1). These salts generally have some water of hydration associated with them, typically on the order of 1 to 6 moles per mole of salt. Most preferably, the aluminum salt is aluminum chlorohydrate (i.e., X is Cl in the above formula), especially 5/6 basic aluminum chlorohydrate where a is about 1, such that the aluminum to chlorine mole ratio is about 1.9:1 to 2.1:1. Aluminum chlorohydrate is referred to as "ACH" herein.

Preferred aluminum-zirconium salts are mixtures or complexes of the above-described aluminum salts with zirconium salts of the formula $ZrO(OH)_{2-pb}Y_b$ wherein Y is Cl, Br, I, $NO_3$, or $SO_4$, b is about 0.8 to 2, and p is the valence of Y. The zirconium salts also generally have some water of hydration associated with them, typically on the order of 1 to 7 moles per mole of salt. Preferably the zirconium salt is zirconyl hydroxychloride of the formula $Zr(OH)_{4-b}Cl_b$ where b is about 0.7 to about 4.0 (which is intended to include the structure sometimes written as $ZrO(OH)_{2-d}Cl_d$ where d is about 1 to 2). The aluminum-zirconium salts encompassed by the present invention have an Al:Zr mole ratio of about 2 to about 10, and a metal:X+Y ratio of about 0.73 to about 2.1, preferably about 0.9 to 1.5. A preferred salt is aluminum-zirconium chlorohydrate (i.e., X and Y are Cl), which has an Al:Zr ratio of about 2 to about 10 and a metal:Cl ratio of about 0.9 to about 2.1. Thus, the term aluminum-zirconium chlorohydrate is intended to include the tri-, tetra-, penta- and octa-chlorohydrate forms, with aluminum-zirconium tetrachlorohydrate being most preferred. Aluminum-zirconium chlorohydrate is referred to as "AZCH" herein. An especially preferred aluminum-zirconium chlorohydrate is one having a low M:Cl ratio, typically from about 0.9:1 to about 1.2:1 (see, for example, U.S. Pat. No. 4,331,609). Generally, the aluminum-zirconium antiperspirant salts also contain a neutral amino acid such as glycine, typically in an amount to provide a Zr:Gly ratio of about 1:1 to about 1:4.

The preferred aluminum and aluminum-zirconium salts for use in compositions of the present invention are of the enhanced efficacy type. The enhanced efficacy salts provide higher sweat reduction than standard salts and are typically differentiated from conventional antiperspirant salts by reference to the various aluminum peaks that can be identified when the salt is analyzed by size exclusion chromatography, typically HPLC (high pressure liquid chromatography), of 10% aqueous salt solutions. A suitable chromatographic technique must be capable of resolving the Al into at least four distinct peaks (labeled peaks 2 (or 1+2), 3, 4 and 5), such as is shown in U.S. Pat. No. 5,330,751. One type of enhanced efficacy salt has been described as having an increased peak 4 content or an increased peak 4 to peak 3 ratio compared to conventional salts. (In some cases, enhanced salts have been described as having increased "band III" content by some authors, depending on the chromatographic technique and nomenclature employed. Generally, bands I, II, III and IV of one system correspond to peaks 1+2 (band I), 3, 4 and 5 of the other system.) Typically, the known enhanced efficacy salts (measured as 10% solutions) have an HPLC peak 4 to peak 3 area ratio of 0.5 or higher, preferably at least 0.7, with at least 70%, preferably at least 80%, of the aluminum contained in peaks 3 and 4. (The aluminum present in peaks 3 and 4 should be of the $Al^c$ type, not $Al^b$, when analyzed by the ferron test.) Thus, the enhanced salts will typically have a peak 4 content of at least 30% of the total aluminum contained in all the peaks (measured by peak area). In contrast, conventional non-enhanced antiperspirant salts have a negligible peak 4 content or a peak 4 to 3 area ratio less than 0.2, typically about 0.1.

A new type of enhanced efficacy aluminum-zirconium antiperspirant salt has been recently described in U.S. Pat. No. 6,436,381 in which at least 33%, preferably at least 45%, of the aluminum is found in HPLC peak 5. This salt may have even greater efficacy than the aforementioned high peak 4 salts. Enhanced efficacy aluminum chlorohydrate is referred to as "EACH" herein. Enhanced efficacy aluminum-zirconium chlorohydrate with high peak 4 content is referred to as "EAZCH" herein. Enhanced efficacy aluminum-zirconium chlorohydrate with high peak 5 content is referred to as "$E^5AZCH$" herein.

Since the most effective antiperspirant salts currently in use are the enhanced efficacy aluminum-zirconium salts, the compositions of the present invention will preferably contain such salts, most preferably enhanced efficacy aluminum-zirconium chlorohydrate (either the high peak 4 or high peak 5 type). Furthermore, such compositions should ideally contain the maximum amount of such salts that can be reasonably included within FDA guidelines without detracting from the application aesthetics of the final composition. Thus, the composition will ideally contain about 13% to about 26% by weight of the aluminum-zirconium salt (which corresponds to about 10%–20% active (USP)).

The compositions of the present invention may optionally include a water soluble calcium salt, such as calcium chloride. It has been recently suggested that the inclusion of a water soluble calcium salt may boost antiperspirant efficacy. The water soluble calcium salt may be included as part of the antiperspirant salt, as described in U.S. Pat. No. 6,042,816, or it may be added separately to the formulation, as described in U.S. Pat. No. 5,955,065, where it will typically comprise about 1% to about 12% by weight.

The antiperspirant composition may also include a deodorant active in one portion or in both portions. A suitable deodorant active may be any agent that inhibits, suppresses, masks or neutralizes malodor. These may include (1) antimicrobial or bactericidal agents which kill the bacteria responsible for malodor production, (2) agents which inhibit or suppress or interfere with the bacterial enzymatic pathway that produces malodor, or (3) agents which mask or absorb or neutralize malodor. Fragrances, encapsulated fragrances, or fragrance precursors which produce fragrances in the underarm are not considered deodorant active agents for purposes of this invention. Examples of deodorant actives include cetyl pyridinium chloride, 2,4,4'- trichloro-2'-hydroxy diphenyl ether (triclosan), 3,4,4'-trichlorocarbanilide (triclocarban), usnic acid salts, zinc phenolsulfonate, zinc citrate, zinc pyrithione, β-chloro-D-alanine, D-cycloserine, aminooxyacetic acid, cyclodextrin, sodium bicarbonate, etc. Aluminum and aluminum-zirconium antiperspirant salts, while not preferred for this purpose, can also function as deodorant active agents when used at relatively low levels (e.g., less than 6% by weight). When included in the composition, a deodorant active will generally comprise, by weight of the total composition, about 0.01% to about 10%, preferably about 0.1% to about 6%. The deodorant active may be included as a free oil or in encapsulated form for controlled release.

Each portion of the antiperspirant composition further includes a dermatologically acceptable, water-immiscible liquid carrier vehicle (as hereinafter described), the first portion including a first hydrophobic carrier vehicle and the second portion including a second hydrophobic carrier vehicle. The first hydrophobic carrier vehicle and the second hydrophobic carrier vehicle may be comprised of the same or different material(s). However, in order to minimize migration of components from one portion to the other portion, it is preferred that the second hydrophobic carrier vehicle is comprised of substantially the same material(s) as the first hydrophobic carrier vehicle. It is even more preferred that the second hydrophobic carrier vehicle is comprised of substantially the same material(s) in substantially the same proportions as the first hydrophobic carrier vehicle. While the hydrophobic carrier vehicle may include some small amount of a lower alkanol, such as ethanol, or a polyhydric alcohol, such as propylene glycol, it is preferred that the hydrophobic carrier vehicle is substantially free (that is, contains less than 2%, preferably less than 1%, and most preferably less than 0.1%) of lower alkanol and polyhydric alcohol. The hydrophobic carrier vehicle will typically comprise about 35% to about 99%, preferably about 40% to about 90%, by weight, of each portion.

The water-immiscible liquid carrier vehicle will comprise one or more hydrophobic materials which are liquid at 20° C. Materials suitable for use include any of the silicone oils and organic oils commonly utilized in the formulation of anhydrous topical antiperspirant compositions. Silicone oils include the volatile silicones, which evaporate quickly and provide a dry feel, and the non-volatile silicones, which provide emolliency.

The volatile silicones include the cyclic polydimethylsiloxanes, also known as cyclomethicones, which have from about 3 to about 7 silicon atoms, and the linear polydimethylsiloxanes, also known as dimethicones, which have from about 2 to about 8 silicon atoms. The linear volatile silicones generally have viscosities of less than 5 cs ($5 \times 10^{-6}$ m$^2$/sec) at 25° C., while the cyclic volatile silicones have viscosities under 10 cs ($10^{-5}$ m$^2$/sec). Mixtures of volatile silicones may be advantageously employed. Examples of volatile silicones include DC 245 and DC 200 (1.0 cs).

The non-volatile silicones will typically have a viscosity of about 5 to about 1000 cs ($5-1000 \times 10^{-6}$ m$^2$/sec), preferably about 10 to 500 cs ($10-500 \times 10^{-6}$ m$^2$/sec), and include polyalkylsiloxanes such as dimethicone (e.g., DC 200), polyphenylsiloxanes (e.g., DC 710 or DC 555) and polyalkylarylsiloxanes such as phenyltrimethicone (e.g., DC 556).

Silicon-free organic oils that are liquid at 20° C. and relatively hydrophobic can be included instead of, or in addition to, the silicone oils. The organic oils include liquid aliphatic hydrocarbons such as mineral oil, hydrogenated polyisobutene, polydecene, paraffins and isoparaffins; liquid aliphatic alcohols such as octyldodecanol and isostearyl alcohol; liquid fatty alcohol esters such as $C_{12-15}$ alkyl benzoate, $C_8$ alkyl benzoate, isostearyl benzoate, octyldodecyl benzoate and myristyl octanoate; liquid fatty acid esters such as isopropyl palmitate, isopropyl myristate, isostearyl isostearate and octyl isononanoate; liquid dicarboxylic acid esters such as diisopropyl sebacate; liquid polypropylene glycol ethers of $C_{4-20}$ alcohols such as PPG-10 butanediol, PPG-14 butyl ether, PPG-5-Buteth-7 and PPG-3-Myreth-3; and alkylmethoxy cinnamates such as octylmethoxy cinnamate. Preferred organic oils include $C_{12-15}$ alkyl benzoate and $C_8$ alkyl benzoate.

Preferably, at least one of the oils in the hydrophobic carrier vehicle will have a relatively high refractive index (i.e., a refractive index greater than about 1.45, preferably greater than about 1.46). More particularly, such high refractive index oil will comprise at least 20%, preferably at least 30%, and most preferably at least 40% of the total hydrophobic carrier vehicle, by weight. The high refractive index oil helps to reduce the amount of visible residue (i.e., less whitening) left by the product with use and, more importantly, increases the average refractive index of the hydrophobic carrier vehicle so that it can be matched to the refractive index of the gelling agent. Such matching of refractive indices is useful to achieve a translucent to transparent second portion, as described later, and a more aesthetically pleasing first portion.

Each portion of the antiperspirant composition also includes a gelling agent (as hereinafter described), the first portion including a first gelling agent and the second portion including a second gelling agent. The first gelling agent and the second gelling agent may be comprised of the same or different material(s). However, it is preferred that the second gelling agent is comprised of substantially the same material(s) as the first gelling agent. It is even more preferred that the second gelling agent is comprised of substantially the same material(s) in substantially the same proportions as the first gelling agent.

The gelling agent may be any material or mixture of materials that may be dissolved or dispersed into the selected hydrophobic carrier vehicle at elevated temperature (e.g., >50° C.) to form a homogeneous solution or dispersion and which will substantially thicken or harden the vehicle upon cooling to form a non-flowable solid, soft-solid, gel or cream at room temperature (about 25° C.). Excluded from potential gelling agents, as used herein, are the dibenzylidene alditols, such as dibenzylidene sorbitol, and the fatty acid soaps, such as sodium stearate, both of which are typically used only in conjunction with polyhydric alcohol vehicles. Preferably the gelling agent will be a material capable of forming a transparent to translucent product with the selected hydrophobic carrier vehicle (e.g., by matching refractive indices of the gelling agent to the hydrophobic carrier vehicle as described later).

Materials which may be suitable for use as gelling agents may be selected from one or more of the following:
polysaccharide esters of fatty acids such as, for example, dextrin palmitate (RHEOPEARL KL or FL), dextrin laurate and dextrin behenate; polyamides such as VERSAMID 950 (Henkel) derived from hexamethylene diamine and adipic acid; hydroxy fatty acids, such as 12-hydroxystearic acid, and esters and amides thereof (e.g., 12-hydroxystearic acid benzyl ester and 12-hydroxystearic acid isopropylamide); N-acyl amino acid amides such as N-lauroylglutamic acid di-n-butyl amide (LGB, Dow Amerchol, or GP-1, Ajinomoto) and N-stearoylglutamic acid dihexylamide; fatty amides such as, for example, Stearamide MEA and Lauramide DEA; alkyl amides such as 2-dodecyl-N,N'-dibutylsuccinamide; sterols, such as lanosterol, β-sitosterol and campesterol, and sterol esters, such as oryzanol, particularly when used in combination; triglycerides such as tribehenin (SYNCHROWAX HR-C), tristearin, trihydroxystearin (THIXCIN), hydrogenated castor oil (castor wax), and hydrogenated high erucic acid rapeseed oil (HEAR oil); cellobiose fatty acid esters such as cellobiose octanonanoate; waxes such as polyethylene homopolymers (particularly MWt.=300–2000) and long chain esters such as $C_{16-22}$ alkylstearate behenate (K80P, Koster Keunen); fatty alcohols having from 14–40 carbon atoms such as stearyl alcohol, behenyl alcohol and $C_{20-40}$ alcohol; oil-soluble polymeric gellants such as ethylene-propylene-styrene copolymers or butylene-ethylene-styrene copolymers (e.g., Versagels, Penreco); and silicone waxes such as C30–45 alkyl dimethicone (GE SF1642). The foregoing list of materials is illustrative only and non-limiting. Other types of gelling agents also may be suitable for use. A preferred gelling agent will include at least one of 12-hydroxystearic acid or N-lauroylglutamic acid di-n-butyl amide, most preferably both of these in combination.

It is highly desirable that the second portion of the antiperspirant composition is translucent to transparent for optimum aesthetic appearance. To achieve this, the second hydrophobic carrier vehicle should have an average refractive index that approximately matches the refractive index of the second gellant. Ideally, the average refractive indices of the vehicle and gellant should match to about 0.05 or better, preferably about 0.04 or better, more preferably about 0.03 or better, most preferably about 0.02 or better. To achieve a transparent appearance, the average refractive indices of the vehicle and gellant should match to about 0.001 or better, preferably about 0.0005 or better. For optimum aesthetic appearance, it is also preferred that the first hydrophobic carrier vehicle has an average refractive index that approximately matches the refractive index of the first gellant. However, this will not make the first portion translucent because of the presence of the antiperspirant salt that is suspended therein.

When referring to the average refractive index of the vehicle, as used herein, this means the refractive index of the vehicle including all other components (except, of course, the gelling agent) which are soluble in the vehicle, such as, for example, any liquid emollients, fragrances, skin soothing agents, etc., which are desired to be included in the final formulation. Ideally, the carrier vehicle, whether the first and/or the second, will have an average refractive index of about 1.450 to about 1.500.

Although the gelling agent which is utilized may not have a known or readily available refractive index, it is a simple matter to disperse the gelling agent into a number of oil or oil mixtures of differing refractive index, then determine which dispersion is transparent. The refractive index of the oil or oil mixture that provides a transparent dispersion will thus approximate the refractive index of the gelling agent. If the desired gelling agent is a mixture of two materials, then obviously those two materials should have refractive indices that are relatively close so that the refractive index of the vehicle will approximately match both gelling agent materials.

The foregoing list of materials is by way of example only and is not intended to be a comprehensive list of all potential materials that may be useful in an antiperspirant composition. Obviously, the skilled worker may select materials which provide the desired application and aesthetic characteristics of the particular form of antiperspirant composition to be produced. For example, the antiperspirant composition will ideally include a fragrance and/or an encapsulated fragrance. Also, at least one portion, preferably the second portion, will include a colorant. In addition, it may be desirable to include, in at least one portion, a surfactant or wash-off agent (typically, an ethoxylated fatty acid or alcohol such as, for example, PEG-8 distearate or C20–40 Pareth-10). It will be apparent to the skilled worker that various other components known to be suitable for use in topical compositions may also be included as desired.

The topical antiperspirant composition of the present invention may be formulated as a cream or gel, soft-solid or solid stick. A solid stick is preferred. The solid stick will preferably have a hardness of about 100 to 600 grams, preferably about 150 to 500 grams, most preferably about 200 to 400 grams. Stick hardness is measured in grams using a TA-XT2 Texture Analyzer from Texture Technologies Corp. with a cone-shaped needle (TA-17, 30° cone), a cursor speed of 1.0 mm/sec and a penetration distance of 5 mm.

The present invention may be further illustrated by the following examples in which the parts and percentages are by weight.

EXAMPLES 1 to 3

Solid Stick Antiperspirant

Solid stick antiperspirant compositions, having the construction depicted in FIGS. 1–2, are prepared having the ingredients and the amounts set out below. Each of these compositions is prepared as follows: The first (or outer) portion is prepared by mixing the carrier vehicle components (cyclomethicone, $C_{12-15}$ alkyl benzoate, phenyl trimethicone, isopropyl myristate) with the surfactant (C20–40 Pareth-10) and the gelling agent (12-HSA and LGB) and heating the mixture to 100° C. until homogeneous. After cooling the mixture to 75° C., the antiperspirant salt (EAZCH) is added, then the fragrance(s) are added below about 70° C. The completed formulation is cooled to about 65° C., then poured into a stick form mold around a centrally located, removable rectangular insert, which occupies about 33% of the mold volume. The mold is cooled to harden the outer portion, then the removable insert is removed to leave a rectangular central cavity in the hardened outer portion, which cavity will become the inner (or stripe) portion once the second portion is added.

The second (or stripe) portion is prepared in a manner similar to the first portion except that it does not contain any antiperspirant salt or surfactant. The colorant and fragrance (s) are added at about 65° C. The completed formulation is cooled to about 60° C. and poured into the aforementioned central cavity, where it hardens to form a translucent colored stripe between and contiguous with the two outer white opaque portions.

| Ingredient | Weight Percent | | |
|---|---|---|---|
| | Ex. 1 | Ex. 2 | Ex. 3 |
| First Portion (Outer) | | | |
| Cyclomethicone (DC 245) | 36.00 | 17.20 | 2.60 |
| $C_{12-15}$ Alkyl Benzoate[1] | 9.15 | 28.60 | 31.30 |
| Isopropyl myristate | | | 15.62 |
| Phenyl trimethicone (DC 556) | | | 2.60 |
| 12-Hydroxystearic acid | 12.00 | 12.00 | 6.00 |
| LGB[2] | 2.50 | 2.00 | 1.35 |
| C20–40 Pareth-10[3] | 3.00 | 3.00 | 3.00 |
| EAZCH[4] | 33.50[4] | 33.50 | 33.50 |
| Fragrance | 3.85 | 3.70 | 4.03 |
| Second Portion (Stripe) | | | |
| Cyclomethicone (DC 245) | 36.00 | 30.70 | 4.30 |
| $C_{12-15}$ Alkyl Benzoate[1] | 46.55 | 51.02 | 51.78 |
| Isopropyl myristate | | | 25.85 |
| Phenyl trimethicone (DC 556) | | | 4.30 |
| 12-Hydroxystearic acid | 15.00 | 15.44 | 10.00 |
| LGB[2] | 1.50 | 1.50 | 2.00 |
| Colorant | 0.10 | 0.10 | 0.07 |
| Fragrance | 0.85 | 1.24 | 1.70 |

[1] Finsolv TN (Finetex Inc.)
[2] N-lauroyl glutamic acid di-n-butylamide (Dow/Amerchol)
[3] Performathox 450 (New Phase Technologies)
[4] Enhanced Al—Zr Chlorohydrate Gly; approximately 17.5% USP active in total composition

What is claimed is:

1. A non-flowable anhydrous topical antiperspirant composition comprising a first portion and a second portion contiguous with the first portion, the first portion being semi-opaque to opaque and comprising a first hydrophobic carrier vehicle and a first gellant and having a particulate antiperspirant active suspended therein, and the second portion being translucent to transparent and comprising a second hydrophobic carrier vehicle and a second gellant, wherein the second portion is substantially free of antiperspirant active and other opacifying material, and wherein the second hydrophobic carrier vehicle has an average refractive index that approximately matches the refractive index of the second gellant.

2. The composition of claim 1 wherein the first portion has a % opacity of 61% to 100% and the second portion has a % opacity of 0% to 60%.

3. The composition of claim 2 wherein the second portion has a % opacity of 0% to 50%.

4. The composition of claim 1 wherein the first hydrophobic carrier vehicle has an average refractive index that approximately matches the refractive index of the first gellant.

5. The composition of claim 1 wherein the second hydrophobic carrier vehicle has an average refractive index that matches the refractive index of the second gellant to about 0.05 or better.

6. The composition of claim 1 wherein the second hydrophobic carrier vehicle has an average refractive index that matches the refractive index of the second gellant to about 0.03 or better.

7. The composition of claim 1 wherein the second hydrophobic carrier vehicle and the second gellant are comprised of substantially the same materials in substantially the same proportions as the first hydrophobic carrier vehicle and the first gellant.

8. The composition of claim 1 wherein the second hydrophobic carrier vehicle has an average refractive index of about 1.450 to about 1.500.

9. The composition of claim 8 wherein the first hydrophobic carrier vehicle has an average refractive index of about 1.450 to about 1.500.

10. The composition of claim 1 wherein the first gellant and the second gellant each comprise 12-hydroxystearic acid or n-lauroyl-glutamic acid di-n-butylamide or a mixture thereof.

11. The composition of claim 9 wherein the first gellant and the second gellant each comprise 12-hydroxystearic acid or n-lauroyl-glutamic acid di-n-butylamide or a mixture thereof.

12. The composition of claim 1 wherein the first gellant and the second gellant each comprise polyethylene homopolymer.

13. The composition of claim 1 wherein the first portion comprises 15% to 85%, by volume, of the composition and the second portion comprises 15% to 85%, by volume, of the composition.

14. The composition of claim 1 wherein the first portion comprises 50% to 80%, by volume, of the composition and the second portion comprises 20% to 50%, by volume, of the composition.

15. The composition of claim 1 wherein the composition has an application surface and the second portion forms a geometric shape at the application surface, which geometric shape is bordered on at least one side by the first portion.

16. The composition of claim 1 wherein the composition has an application surface and the second portion forms a geometric shape at the application surface, which geometric shape is bordered on at least two sides by the first portion.

17. The composition of claim 16 wherein the second portion is in the form of a substantially rectangular stripe at the application surface.

18. The composition of claim 17 wherein the stripe extends at least partially downward from the application surface.

19. The composition of claim 15 wherein the second portion is surrounded by the first portion at the application surface.

20. The composition of claim 16 wherein the second portion comprises a plurality of swirled portions interspersed throughout the first portion to provide a marbled appearance.

21. A method of reducing perspiration from human skin comprising applying to human skin a topical antiperspirant composition according to any one of claims 1 to 20.

* * * * *